United States Patent [19]

Gugel et al.

[11] 4,385,523
[45] May 31, 1983

[54] APPARATUS FOR TESTING THE WALLS OF VESSELS

[75] Inventors: Georg Gugel, Kalchreuth; Franz Huber, Erlangen, both of Fed. Rep. of Germany

[73] Assignee: Kraftwerk Union Aktiengesellschaft, Mülheim, Fed. Rep. of Germany

[21] Appl. No.: 346,882

[22] Filed: Feb. 8, 1982

Related U.S. Application Data

[63] Continuation of Ser. No. 242,180, Mar. 10, 1981, abandoned, which is a continuation of Ser. No. 95,080, Nov. 16, 1979, abandoned.

[30] Foreign Application Priority Data

Nov. 16, 1978 [DE] Fed. Rep. of Germany ....... 2849763

[51] Int. Cl.³ ............................................. G01N 29/04
[52] U.S. Cl. ...................................... 73/640; 376/249
[58] Field of Search ................. 73/640, 635, 636, 637, 73/638, 622; 324/238, 240, 220; 376/249

[56] References Cited

U.S. PATENT DOCUMENTS

| 3,934,457 | 1/1976 | Clark et al. | 73/637 |
| 3,943,756 | 3/1976 | Aubert et al. | 176/19 R |
| 3,988,922 | 11/1976 | Clark et al. | 73/367 |
| 4,117,733 | 10/1978 | Gugel | 73/640 |

Primary Examiner—Anthony V. Ciarlante
Attorney, Agent, or Firm—Herbert L. Lerner; Laurence A. Greenberg

[57] ABSTRACT

Apparatus for testing vessel walls having projections with a multiplicity of guide tracks extending among the projections for guiding a slide carrying a testing device, and carriage means for transposing the slide onto the individual guide tracks, the carriage means being movable on a transport track connecting the ends of the guide tracks, including a thrust hose rigid in tension and compression and guidable by the guide tracks, respectively, a drive for the thrust hose mounted on the carriage, the thrust hose connecting the slide to the drive, and a jib carried by the carriage and operatively associated with the drive, the jib being of such dimension as to accommodate the slide and the testing device and being movable for adjusting to the guide tracks.

11 Claims, 6 Drawing Figures

APPARATUS FOR TESTING THE WALLS OF VESSELS

This is a continuation of application Ser. No. 242,180, filed Mar. 10, 1981, now abandoned, which is a continuation of Ser. No. 95,080, filed Nov. 16, 1979, now abandoned.

The invention relates to apparatus for testing vessel walls having projections with a multiplicity of guide tracks extending among the projections for guiding a slide carrying a testing device, and a carriage for transposing the slide onto the individual guide tracks, the carriage being movable on a transport track connecting the ends of the guide tracks.

Such an apparatus is described in co-pending application Ser. No. 58,423 of Dietgar Figihuber, Johanes Galiwis, Robert Weber and Jakob Weber, filed on July 18, 1979, and assigned to the same assignee as that of the instant application, wherein the vessel is a cylindrical reactor pressure tank of a boiling-water reactor from which steam and feedwater lines extend as projections. Tracks extend vertically along generatrix lines and pass with the ends thereof in a U-shape over a shielding wall surrounding the reactor pressure vessel. A carriage for transposing the testing device is seated behind the shielding wall and is of relatively large construction since a relatively large space is available between the reactor pressure vessel and the shielding wall.

It is an object of the invention, however, to provide apparatus for testing vessel walls where only a relatively little amount of such space is available as is the case, especially, in the region of the stubs for control-rod drives which are located close to one another on the cover of a pressurized water reactor.

With the foregoing and other objects in view, there is provided in accordance with the invention, an apparatus for testing vessel walls having projections with a multiplicity of guide tracks extending among the projections for guiding a slide carrying a testing device, and carriage means for transposing the glide onto the individual guide tracks, the carriage means being movable on a transport track connecting the ends of the guide tracks, including a thrust hose rigid in tension and compression and guidable by the guide tracks, respectively, a drive for the thrust hose mounted on the carriage, the thrust hose connecting the slide to the drive, and a jib carried by the carriage and operatively associated with the drive, the jib being of such dimension as to accommodate the slide and the testing device and being movable for adjusting to the guide tracks.

In the invention, the slide has only guidance functions, whereas the drive is associated with the carriage. Thus, the slide can be constructed in a considerably more space-saving manner. A compact construction is attained similar to that which is known for the testing of the tubes of steam generators in nuclear power plants. In the latter case, however, no tracks are provided to extend among the projections because the eddy-current probes are directly introduced into the tubes per se.

In accordance with another feature of the invention, the apparatus includes a wind-up-drum for the thrust hose, the jib being connected to the drum. The thrust hose can thus be wound up on the drum and stored. In addition, the drum can serve as a drive member if it is set in motion in the desired direction by a motor. The thrust hose may also be displaced by engaging it at another location thereof, for example, with a pair of friction wheels.

In accordance with a further feature of the invention, the guide tracks, respectively, are formed as a slotted tube enclosing the thrust hose. Guidance for the thrust hose is thereby simultaneously attained. In addition, such tracks afford exceptional protection against soiling so that maintenance requirements are low, which is especially advantageous for nuclear power plants which are of such limited accessibility because of radioactivity. The cross section of the tubes may be circular or polygonal, and especially quadrilateral or rectangular in shape.

In accordance with an added feature of the invention, the thrust hose encloses or surrounds measuring and supply lines. Such measuring lines are primarily electric cables which connect the testing device, preferably one or more ultrasonic measuring heads, to an indicating and/or recording instrument. The supply lines may be, for example, bases for a coupling medium, such as water, especially, but also compressed-air hoses or the like.

In accordance with an additional feature of the invention, the apparatus includes a control track disposed adjacent the transport track, the jib being coupled to the control track for alignment thereof on the guide tracks. This is especially applicable when a multiplicity of tracks is provided. The coupling may be an articulating connection to a guidance slide traveling on the control track.

In accordance with yet other features of the invention, the control track has markings thereon, such as boron formed therein, for alignment thereof with the guide tracks. The slide may not only be portioned in accordance with such markings, but may also be clamped at individual locations, for example, pneumatically, so that the jib may be readily aligned or oriented on the tracks.

Not only do the tracks extend parallel to one another along generatrix lines, as described in the hereinaforementioned co-pending application, but rather, further in accordance with the invention, the guide tracks form an intersecting network, the jib being fastened to the carriage so as to be pivotable about at least the angle or intersection. Thus, an especially dense coverage of a vessel wall studded or cleft by projections is achievable. Also, in accordance with the invention, the guide tracks are interrupted in vicinity of the points of intersection, the jib having a length which is a multiple of the length of the respective interruptions. With the just-mentioned ratio of length the slide can pass by or overcome the interruptions without any appreciable loss of guidance and yet be taken up satisfactorily by the jib if it is to be transposed from one track to another.

In accordance with yet further features of the invention, the slide is formed of a plurality of parts connected articulatingly to one another, the testing device being mounted on one of the parts facing toward the jib. Due to the articulating construction, the curvature of the tracks may be matched, as is required, for example, because of the curvature of the hereinaforementioned cover of a reactor pressure tank, the front or leading parts of the slide facing away from the jib being concerned with the guidance, whereas the parts of the slide facing towards the jib serving to carry the testing device. To this end, and in accordance with a concomitant feature of the invention, a part of the slide facing away from the jib is pointed and has at least one guide roller preventing twisting of the slide about the longitudinal axis of the guide tracks.

Other features which are considered as characteristic for the invention are set forth in the appended claims.

Although the invention is illustrated and described herein as embodied in apparatus for testing the walls of a vessel, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings, in which.

Figure 1:
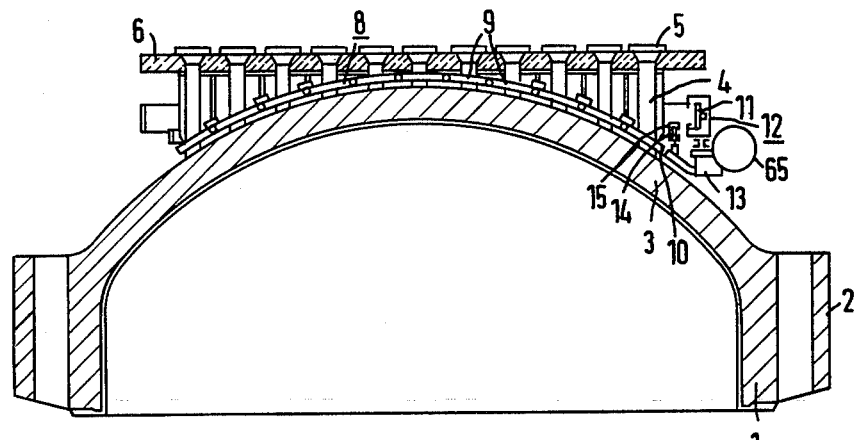
FIGS. 1 and 2 are respective vertical sectional and top plan views of the cover of a reactor pressure vessel of a pressurized water reactor.
Figure 3:
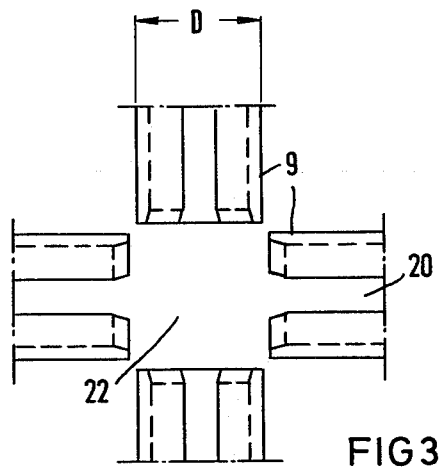
FIGS. 3 and 4 are enlarged fragmentary top plan and elevational, though partly sectional views, respectively, of FIGS. 1 and 2 showing the rails or tracks thereof.
Figure 4:
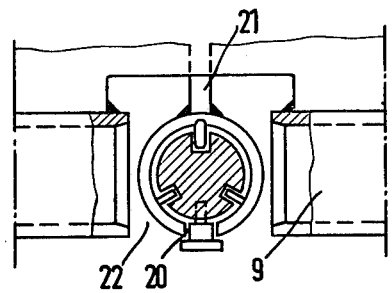
Figure 5:
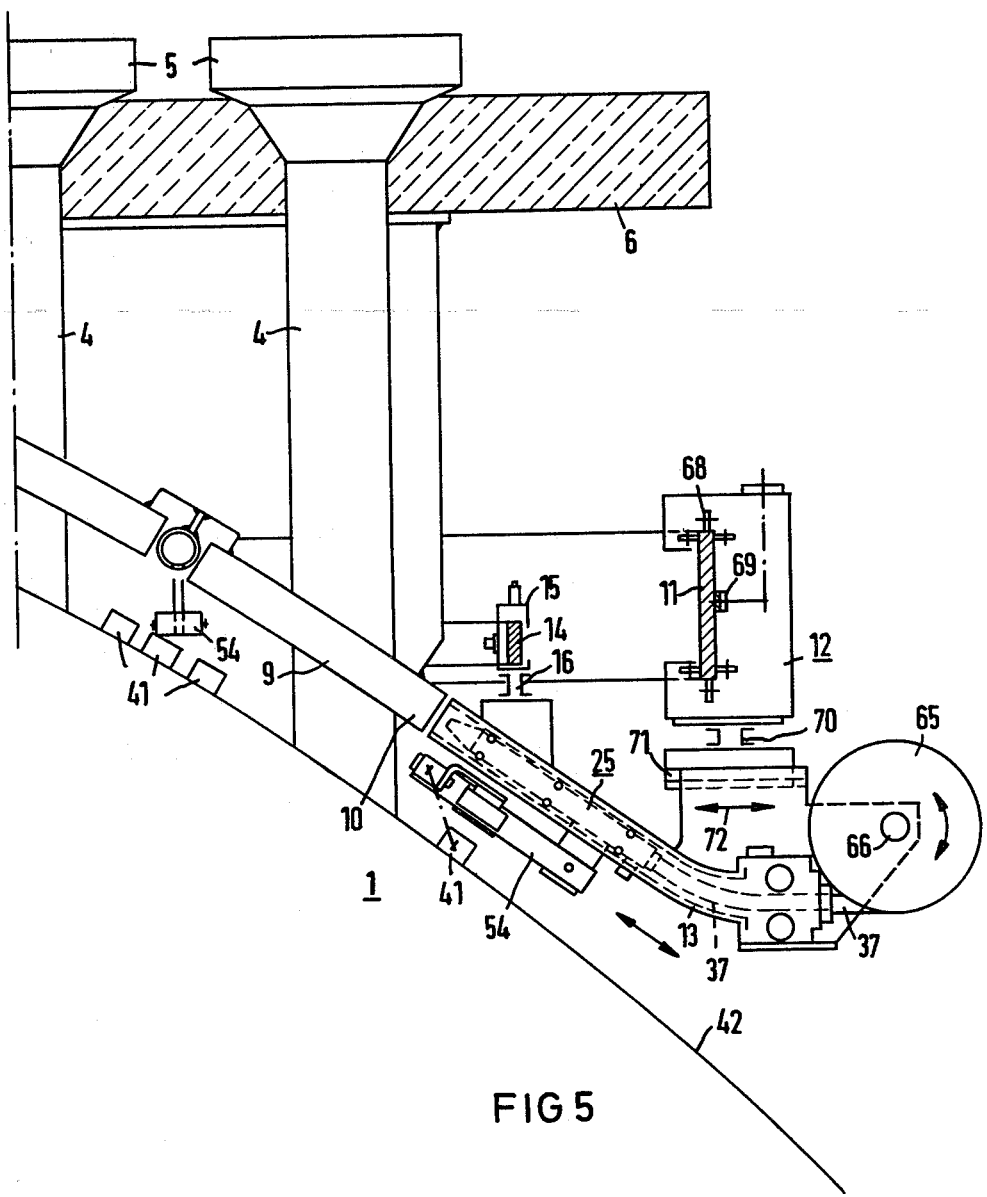
Figure 6:
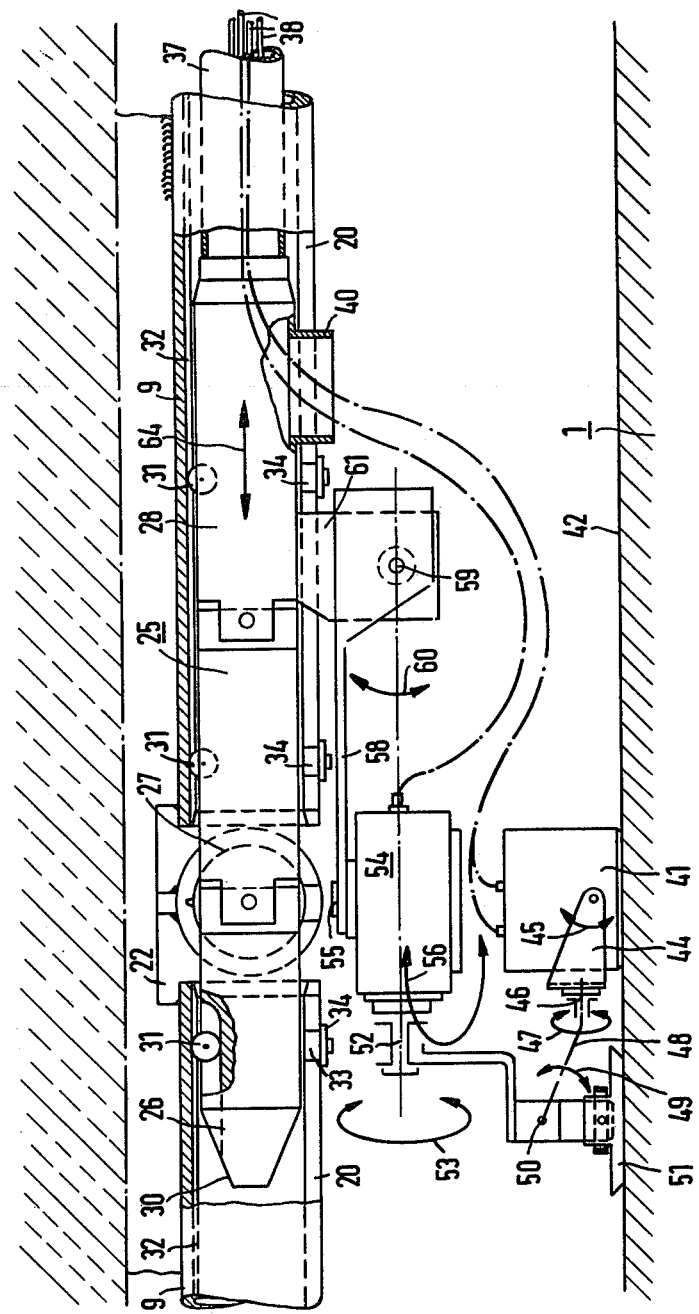

FIG. 5 is a fragmentary enlarged view similar to that of FIG. 1 of the upper right hand side of the latter figure showing in greater detail a carriage employed for transporting a testing-device slide from track to track in accordance with the invention; and FIG. 6 is an elevational and partly vertical-sectional view enlarged to the scale of FIGS. 3 and 4 of the slide together with a testing device.

Figure 2:
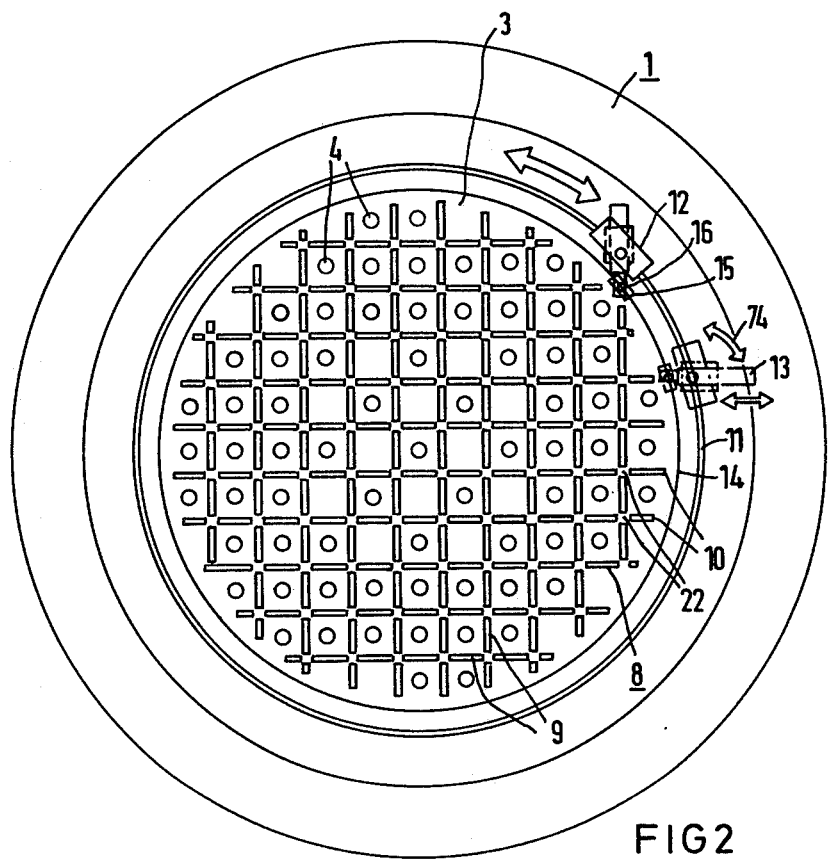

Referring now to the drawing and first, particularly, to FIG. 1 thereof, there is shown a cover 1 of a reactor pressure vessel having a diameter, for example, of four meters and formed with a convex or domed region 3 projecting upwardly beyond a flange 2. Stubs 4 for control rod drives are provided on the domed region of the cover 1 and, as further shown in FIG. 2, are arranged in regular distribution. The stubs 4 terminate with flanges 5 which are disposed in one plane, and are provided with an insulating layer 6 to afford thermal insulation.

Due to the stubs 4, the strength of the cover 1 is diminished. It is, therefore, essential that the cover 1 be subjected to continuous monitoring or control especially in the region of the stubs 4 by checking with a suitable measuring device, so as to ensure the integrity and pressure-tightness thereof. On the other hand, the cover region is not only virtually inaccessible because of the high temperatures and radiation, but also, the accessibility for testing devices, especially for ultrasonic measurements, is impeded by the stubs 4.

As further shown in FIG. 2, the cover 1, in the domed region 3 thereof at which the stubs 4 are located, is covered with a network 8 of rails or tracks which intersect at right angles and have ends 10 lying approximately on an imaginary circle. The surface of the cover 1 covered by the track network 8 is enclosed by a circular track 11 carrying a carriage 12. The carriage transport 12 has a pivotal boom or jib 13 which is coupled to a control track or rail 14 lying circularly between the track 11 and the network 8 of the tracks 9. A guidance slide 15 is provided to effect the coupling, the jib 13 being coupled therein by means of an articulating joint 16.

The tracks 9 are formed by tubes having a circular cross section and provided at the underside thereof with a slot 20, the tubes forming the tracks 9 being connected by a web or crosspiece 21 (FIG. 4) to the cover 1 of the reactor pressure vessel. The track tubes 9 formed with the slot 20 are interrupted in vicinity of the mutual intersecting points thereof. As shown in FIG. 3, the interruption in the track tubes 9 is somewhat longer than the outer diameter D of the tracks 9, yet is several times smaller than the length of the jib or boom 13.

FIG. 6 shows a slide 25 guidable in the track tube 9 and formed of three parts 26, 27 and 28 articulatingly connected to one another. One of the parts is an outer part 26 formed with a conically pointed region 30. Another of the parts is an adjoining cylindrical part 27 having a guide roller 31 mounted therein which engages in a guidance slot 32 formed in the tracks or rails 9. A diametrically opposing additional guide roller 33 engages in the slot 20 and is formed with a collar 34 which can project beyond the width of the slot 20. At the other end of the slide 25 located opposite and remote from the conical point 30, the other end being in the glide part 28, the slide 25 is connected to a thrust or push hose 37, which is rigid in tension and compression yet is deformed relatively easily in lateral or transverse direction. The thrust hose 37 is formed, for example, of plastic material, such as is known by the trade name TEFLON, which is polytetrafluoroethylene and encloses or surrounds measurement and supply lines 38. In the region of the slide part 28. the lines 38 extend through a frame to projecting into the slot 20 to a test head 41 lying on that surface 42 of the cover 1 that is to be tested or inspected.

The test head 41 is a conventional ultrasonic measuring head and is pivotably mounted in a fork 44 as indicated by the curved double headed arrow 45. The fork 44 is, in turn, supported by an articulating joint 46 pivotably in the directions of the curved double-headed arrow 47 on a lever 48 which is pivotable in the directions of the curved double-headed arrow 49. The lever 48 is seated in an articulating joint 50 on a runner 51 which is disposed on the surface 42. The runner 51 is fastened to a support member 51 with another articulating joint 52 so as to be swingable in the direction of the curved double-headed arrow 53, the holding member 54 per se being pivotable with an articulating joint 52 in the directions of the curved double-headed arrow 56. The support member 54 is seated on an arm 59 which is linked so as to be pneumatically pivotable about a pivot 59 in the directions of the curved double-headed arrow 60. The pivot 50 is located on a strap 61 projecting through the slot 20 and firmly connected to the part 28 of the slide 25.

There is further shown in FIG. 6 that the parts 27 and 28 also are guided with guide rollers 31 and 33 in the slots 32 and 20, respectively, so that the motion in either direction of the double-headed arrow 64, which is afforded by the tracks 9, can be performed without much frictional resistance.

It is apparent from FIG. 5 how the slide 25 is introduced into the jib or boom 13 of the carriage 12. The thrust hose 37 is then almost completely wound onto a drum 65 which is mounted on the jib or boom 13 at 66, and serves as the drive for the slide 25. The carriage 12 can therefore be driven, with the use of a toothed rack 67 controllably on the transport track 11, which has a rectangular cross section, whereon it is guided by six guide rollers 69. The jib or boom 13 is guided by the control track 14 and is aligned with the next or nearest track 9 so that the slide 25 with the support member 64 and the test head 41 fastened thereto can be transposed.

The matching of the jib or boom 13 to the tracks 9 in accordance with inclination and length is realized due to the fact that the jib or boom 13 is fastened with a pivot 70 to the carriage 12, and, moreover, has a longitudinal guidance device 71, for example, in the form of a lovetail joint. The longitudinal or lengthwise connection affords movements in the direction of the double-headed arrow 72, while the pivot 70 permits swiveling, as indicated by the curved double-headed arrow 74 in FIG. 2.

Besides the hereinaforedescribed testing of the reactor pressure vessel in vicinity of the control-rod stubs, the invention may also be used to particular advantage for testing of pressurizer bottoms in vicinity of the heating-rod stubs as well as at longitudinal welding seams in pipeline elbows or bends in main coolant lines if they are rendered inaccessible due to so-called deflection protection devices at short intervals.

There is claimed:

1. Apparatus for testing vessel walls having projections with a multiplicity of guide tracks extending among the projections for guiding a slide carrying a testing device, and carriage means for transposing the slide onto the individual guide tracks, the carriage means being movable on a transport track connecting the ends of the guide tracks, comprising a thrust hose rigid in tension and compression and guidable by the guide tracks, respectively, a drive for the thrust hose mounted on the carriage, said thrust hose connecting the slide to said drive, and a jib carried by the carriage and operatively associated with said drive, said jib being of such dimension as to accommodate the slide and the testing device and being movable for adjusting to the guide tracks.

2. Apparatus according to claim 1 including a wind-up drum for said thrust hose, said jib being connected to said drum.

3. Apparatus according to claim 1 wherein the guide tracks, respectively, are formed as a slotted tube enclosing said thrust hose.

4. Apparatus according to claim 1 wherein said thrust hose encloses measuring and supply lines.

5. Apparatus according to claim 1 including a control track disposed adjacent the transport track, said jib being coupled to said control track for alignment thereof on the guide tracks.

6. Apparatus according to claim 5 wherein said control track has markings thereon for alignment on the guide tracks.

7. Apparatus according to claim 6 wherein said markings are in the form of bores.

8. Apparatus according to claim 1 wherein the guide tracks form an intersecting network, said jib being fastened to said carriage so as to be pivotable about at least the angle of intersection.

9. Apparatus according to claim 8 wherein the guide tracks are interrupted in vicinity of the points of intersection, said jib having a length which is a multiple of the length of the interruption.

10. Apparatus according to claim 1 wherein the slide is formed of a plurality of parts connected articulatingly to one another, said testing device being mounted on one of said parts facing toward said jib.

11. Apparatus according to claim 10 wherein a part of said slide facing away from said jib is pointed and has at least one guide roller preventing twisting of the slide about the longitudinal axis of the guide tracks.

* * * * *